(12) United States Patent
Raz

(10) Patent No.: US 6,463,425 B2
(45) Date of Patent: *Oct. 8, 2002

(54) NEURAL NETWORK ASSISTED MULTI-SPECTRAL SEGMENTATION SYSTEM

(75) Inventor: Ryan S. Raz, Toronto (CA)

(73) Assignee: Morphometrix Technologies Inc., Toronto (CA)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/040,378

(22) Filed: Mar. 18, 1998

(65) Prior Publication Data

US 2002/0042785 A1 Apr. 11, 2002

Related U.S. Application Data

(63) Continuation of application No. PCT/CA96/00619, filed on Sep. 18, 1996.
(60) Provisional application No. 60/003,964, filed on Sep. 19, 1995.

(51) Int. Cl.[7] .................................................. G06N 3/02
(52) U.S. Cl. .............................. 706/20; 382/128; 435/7
(58) Field of Search ........................ 706/20; 382/128; 128/632; 435/7

(56) References Cited

U.S. PATENT DOCUMENTS

| | | | |
|---|---|---|---|
| 4,839,807 A | * 6/1989 | Doi et al. ............... | 364/413.13 |
| 4,965,725 A | * 10/1990 | Rutenberg ................. | 382/128 |
| 4,998,284 A | * 3/1991 | Bacus et al. ................. | 382/133 |
| 5,257,182 A | * 10/1993 | Luck et al. .................. | 382/224 |
| 5,276,771 A | 1/1994 | Manukian et al. ............. | 395/24 |
| 5,276,772 A | 1/1994 | Wang et al. .................... | 395/27 |
| 5,331,550 A | 7/1994 | Stafford et al. ......... | 364/413.02 |
| 5,544,650 A | * 8/1996 | Boon et al. ................. | 128/632 |
| 5,726,018 A | * 3/1998 | Pasternack ..................... | 435/6 |
| 5,939,278 A | * 8/1999 | Boon et al. ..................... | 435/7 |

FOREIGN PATENT DOCUMENTS

| | | | |
|---|---|---|---|
| EP | 0 525 964 A | 2/1993 | ............ H04N/1/46 |
| EP | 0 587 093 A | 3/1994 | ........... G06F/15/18 |
| EP | 0 710 004 A | 5/1996 | ............ H04N/1/40 |
| WO | WO91/20048 | 12/1991 | ........... G06F/15/42 |
| WO | WO92/13308 | 8/1992 | ........... G06F/15/00 |

OTHER PUBLICATIONS

Kosko, Bart, Neural Networks and Fuzzy Systems: A Dynamical Systems Approach to Machine Intelligence, Prentice–Hall, Inc., Englewood Cliffs, New Jersey, 1992, pp. 131–137, Jan. 1992.*

(List continued on next page.)

Primary Examiner—Mark R. Powell
(74) Attorney, Agent, or Firm—Ridout & Maybee

(57) ABSTRACT

A neural network assisted multi-spectral segmentation method and system. According to the invention, three images having different optical bands are acquired for the same micrographic scene of a biological sample. The images are processed and a cellular material map is generated identifying cellular material. The cellular material map is then applied to a neural network. The neural network classifies the cellular material map into nuclear objects and cytoplasmic objects by determining a threshold surface in the 3-dimensional space separating the cytoplasmic and nuclear regions. In another aspect, the neural network comprises a hardware-encoded algorithm in the form of a look-up table.

14 Claims, 5 Drawing Sheets

OTHER PUBLICATIONS

Chen, C. H., Fuzzy Logic and Neural Network Handbook, McGraw–Hill, Inc., 1996, pp. 2.12–2.18, Jan. 1996.*

Korn, Granino A., Neural Networks and Fuzzy–Logic Control on Personal Computers and Workstations, The MIT Press, Massachusetts Institute of Technology, 1995, pp. 59–62, Jan. 1995.*

IEEE 1994 National Aerospace & Electronics Conference (NAECON) Dayton, US, May 23–27, vol. 2, pp. 1090–1097 XP000647232; E. Preston et al: "Development of a field–portable imaging system for scene classification using multispectral data fusion algorithms" see p. 1094, left–hand column, line 31–line 34.

* cited by examiner

NEURAL NETWORK ASSISTED MULTI-SPECTRAL SEGMENTATION SYSTEM

This application is a continuation of my co-pending International Patent Application No. PCT/CA96/00619 filed Sep. 18, 1996 which claims benefit of provisional application 60/003,964 filed Sep. 19, 1995.

FIELD OF THE INVENTION

The present invention relates to automated diagnostic techniques in medicine and biology, and more particularly to neural network for multi-spectral segmentation of nuclear and cytoplasmic objects.

BACKGROUND OF THE INVENTION

Automated diagnostic systems in medicine and biology often rely on the visual inspection of microscopic images. Known systems attempt to mimic or imitate the procedures employed by humans. An appropriate example of this type of system is an automated instrument designed to assist a cyto-technologist in the review or diagnosis of Pap smears. In its usual operation such a system will rapidly acquire microscopic images of the cellular content of the Pap smears and then subject them to a battery of image analysis procedures. The goal of these procedures is the identification of images that are likely to contain unusual or potentially abnormal cervical cells.

The image analysis techniques utilized by these automated instruments are similar to the procedures consciously, and often unconsciously, performed by the human cyto-technologist. There are three distinct operations that must follow each other for this type of evaluation: (1) segmentation; (2) feature extraction; and (3) classification.

The segmentation is the delineation of the objects of interest within the micrographic image. In addition to the cervical cells required for an analysis there is a wide range of "background" material, debris and contamination that interferes with the identification of the cervical cells and therefore must be delineated. Also for each cervical cell, it is necessary to delineate the nucleus with the cytoplasm.

The Feature Extraction operation is performed after the completion of the segmentation operation. Feature extraction comprises characterizing the segmented regions as a series of descriptors based on the morphological, textural, densitometric and colorimetric attributes of these regions.

The Classification step is the final step in the image analysis. The features extracted in the previous stage are used in some type of discriminant-based classification procedure. The results of this classification are then translated into a "diagnosis" of the cells in the image.

Of the three stages outlined above, segmentation is the most crucial and the most difficult. This is particularly true for the types of images typically encountered in medical or biological specimens.

In the case of a Pap smear, the goal of segmentation is to accurately delineate the cervical cells and their nuclei. The situation is complicated not only by the variety of cells found in the smear, but also by the alterations in morphology produced by the sample preparation technique and by the quantity of debris associated with these specimens. Furthermore, during preparation it is difficult to control the way cervical cells are deposited on the surface of the slide which as a result leads to a large amount of cell overlap and distortion.

Under these circumstances a segmentation operation is difficult. One known way to improve the accuracy and speed of segmentation for these types of images involves exploiting the differential staining procedure associated with all Pap smears. According to the Papanicolaou protocol the nuclei are stained dark blue while the cytoplasm is stained anything from a blue-green to an orange-pink. The Papanicolaou Stain is a combination of several stains or dyes together with a specific protocol designed to emphasize and delineate cellular structures of importance for pathological analysis. The stains or dyes included in the Papanicolaou Stain are Haematoxylin, Orange G and Eosin Azure (a mixture of two acid dyes, Eosin Y and Light Green SF Yellowish, together with Bismark Brown). Each stain component is sensitive to or binds selectively to a particular cell structure or material. Haematoxylin binds to the nuclear material colouring it dark blue. Orange G is an indicator of keratin protein content. Eosin Y stains nucleoli, red blood cells and mature squamous epithelial cells. Light Green SF yellowish acid stains metabolically active epithelial cells. Bismark Brown stains vegetable material and cellulose.

The combination of these stains and their diagnostic interpretation has evolved into a stable medical protocol which predates the advent of computer-aided imaging instruments. Consequently, the dyes present a complex pattern of spectral properties to standard image analysis procedures. Specifically, a simple spectral decomposition based on the optical behaviour of the dyes is not sufficient on its own to reliably distinguish the cellular components within an image. The overlap of the spectral response of the dyes is too large for this type of straight-forward segmentation.

The use of differential staining characteristics is only the means to the end in the solution to the problem of segmentation. Of equal importance is the procedure for handling the information provided by the spectral character of the cellular objects when making a decision concerning identity.

In the art, attempts have been made to automate diagnostic procedures, however, there remains a need for a system for performing the segmentation process.

BRIEF SUMMARY OF THE INVENTION

The present invention provides a Neural-Network Assisted Multi-Spectral Segmentation (also referred to as the NNA-MSS) method and system.

The first stage according to the present invention comprises the acquisition of three images of the same micrographic scene. Each image is obtained using a different narrow band-pass optical filter which has the effect of selecting a narrow band of optical wavelengths associated with distinguishing absorption peaks in the stain spectra. The choice of optical wavelength bands is guided by the degree of separation afforded by these peaks when used to distinguish the different types of cellular material on the slide surface.

The second stage according to the invention comprises a neural-network (trained on an extensive set of typical examples) to make decisions on the identity of material already deemed to be cellular in origin. The neural network decides whether or not a picture element in the digitized image is nuclear or not nuclear in character. With the completion of this step the system can continue on applying a standard range of image processing techniques to refine the segmentation. The relationship between the cellular components and the transmission intensity of the light images in each of the three spectral bands is a complex and non-linear one. By using a neural network to combine the information from these three images it is possible to achieve a high degree of success in separating the cervical cell from the background and the nuclei from the cytoplasm. A success that would not be possible with a set of linear operations alone.

The diagnosis and evaluation of Pap smears is aided by the introduction of a differential staining procedure called the Papanicolaou Stain. The Papanicolaou Stain is a combination of several stains or dyes together with a specific protocol designed to emphasize and delineate cellular structures of importance to pathological analysis. The stains or dyes included in the Papanicolaou Stain are Haematoxylin, Orange G and Eosin Azure (a mixture of two acid dyes, Eosin Y and Light Green SF Yellowish, together with Bismarck Brown). Each stain component is sensitive to or binds selectively to a particular cellular structure or material. Haematoxylin binds to the nuclear material colouring it dark blue; Orange G is an indicator of keratin protein content; Eosin Y stains nucleoli, red blood cells and mature squamous epithelial cells; Light Green SF yellowish stains metabolically active epithelial cells; Bismarck Brown stains vegetable material and cellulose.

According to another aspect of the invention, three optical wavelength bands are used in a complex procedure to segment Papanicolaou-stained epithelial cells in digitized images. The procedure utilizes standard segmentation operations (erosion, dilation, etc.) together with the neural-network to identify the location of nuclear components in areas already determined to be cellular material.

The purpose of the segmentation is to extract the cellular objects, i.e. to distinguish the nucleus of the cell from the cytoplasm. According to this segmentation the multi-spectral images are divided into two classes: cytoplasm objects and nuclear objects, which are separated by a multi-dimensional threshold t which comprises a 3-dimensional space.

The neural network according to the invention comprises a Probability Projection Neural Network (PPNN). The PPNN according to the present invention features fast training for a large volume of data, processing of multi-modal non-Gaussian data distribution, good generalization simultaneously with high sensitivity to small clusters of patterns representing the useful subclasses of cells. In another aspect, the PPNN is implemented as a hardware-encoded algorithm.

In one aspect, the present invention provides a method for identifying nuclear and cytoplasmic objects in a biological specimen, said method comprising the steps of: (a) acquiring a plurality of images of said biological specimen; (b) identifying cellular material from said images and creating a cellular material map; (c) applying a neural network to said cellular material map and classifying nuclear and cytoplasmic objects from said images.

In second aspect, the present invention provides a system for identifying nuclear and cytoplasmic objects in biological specimen, said system comprising:. (a) image acquisition means for acquiring a plurality of images of said biological specimen; (b) processing means for processing said images and generating a cellular material map identifying cellular material; (c) neural processor means for processing said cellular material map and including means for. classifying nuclear and cytoplasmic objects from said images.

In a third aspect, the present invention provides a hardware-encoded neural processor for classifying input data, said hardware-encoded neural processor comprising: (a) a memory having a plurality of addressable storage locations; (b) said addressable storage locations containing classification information associated with the input data; (c) address generation means for generating an address from said input data for accessing the classification information stored in said memory for selected input data.

A preferred embodiment of the present invention will now be described, by way of example, with reference to the following specification, claims, and drawings.

DETAILED DESCRIPTION OF THE PREFERRED EMBODIMENT

The present invention provides a Neural Network Assisted Multi-Spectral Segmentation (also referred to as NNA-MSS) system and method. The multi-spectral segmentation method is related to that described and claimed in co-pending International Patent Application No. CA96/00477 filed Jul. 18, 1996 and in the name of the applicant.

The NNA-MSS according to the present invention is particularly suited to Papanicolaou-stained gynaecological smears and will be described in this context. It is however to be understood that the present invention has wider applicability to applications outside of Papanicolaou-stained smears.

Figure 1:
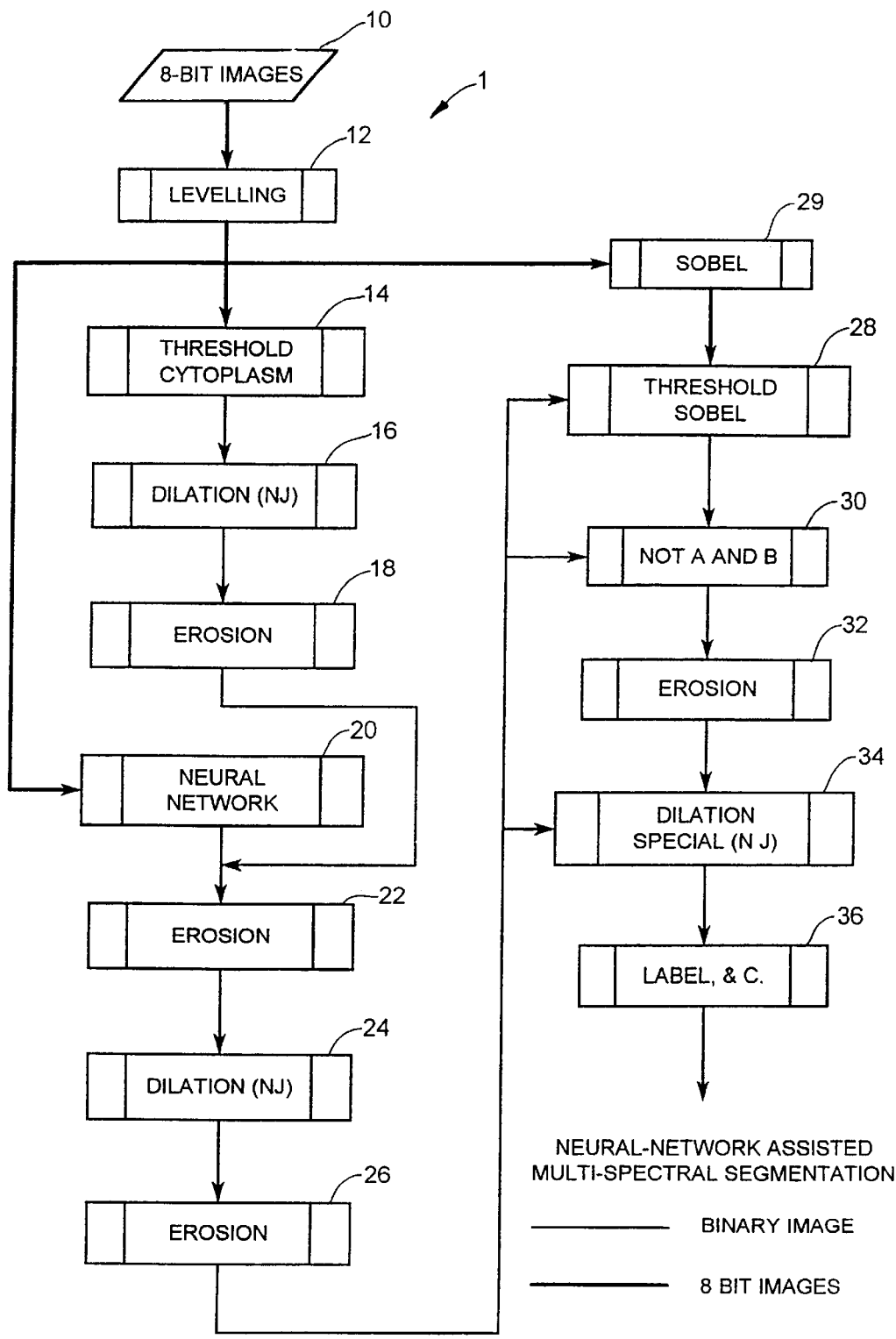
FIG. 1 shows in flow chart form a neural network assisted multi-spectral segmentation method according to the present invention.

Reference is first made to FIG. 1 which shows in flow chart a Neural Network Assisted Multi-Spectral Segmentation (NNA-MSS) method 1 according to the present invention.

The first step 10 involves inputting three digitized images, i.e. micrographic scenes, of a cellular specimen. The images are taken in each of the three narrow optical bands: 540±5 nm; 577±5 nm and 630±5 nm. (The images are generated by an imaging system (not shown) as will be understood by one skilled in the art, and thus need not be described in detail here.) The images are next processed by the multi-segmentation method 1 and neural network as will be described.

As shown in FIG. 1, the images are subjected to a levelling operation (block 12). The levelling operation 12 involves removing the spatial variations in the illumination intensity from the images. The levelling operation is implemented as a simple mathematical routine using known image processing techniques. The result of the levelling operation is a set of 8-bit digitized images with uniform illumination across their fields.

The 8-bit digitized images first undergo a series of processing steps to identify cellular material in the digitized images. The digitized images are then processed by the neural network to segment the nuclear objects from the cytoplasm objects.

Referring to FIG. 1, following the levelling operation 12 the next operation comprises a threshold procedure block 14. The threshold procedure involves analyzing the levelled images in a search for material of cellular origin. The threshold procedure 14 is applied to the 530 nm and 630 nm optical wavelength bands and comprises identifying material in the image of cellular origin as regions of the digitized image that fall within a range of specific digital values. The threshold procedure 14 produces a single binary "map" of the image where the single binary bit identifies regions that are, or are not, cellular material.

The threshold operation 14 is followed by a dilation operation (block 16). The dilation operation 16 is a conventional image processing operation which modifies The binary map of cellular material generated in block 14. The dilation operation allows the regions of cellular material to grow or dilate by one pixel in order to fill small voids in large regions. Preferably, the dilation operation 16 is modified with the condition that the dilation does not allow two separate regions of cellular material to join to make a single region, i.e. a "no-join" condition. This condition allows the accuracy of the binary map to be preserved through dilation operation 16. Preferably, the dilation operation is applied twice to ensure a proper filling of voids. The result of the dilation operations 16 is a modified binary map of cellular material.

As shown in FIG. 1, the dilation operation 16 is followed by an erosion operation (block 18). The erosion operation 18 brings the modified binary map of cellular material (a result of the dilation operation 16) back to its original boundaries. The erosion operation 18 is implemented using conventional image processing techniques. The erosion operation 18 allows the cellular boundaries in the binary image to shrink or erode but will not affect the filled voids. Advantageously, the erosion operation 18 has the additional effect of eliminating small regions of cellular material that are not important to the later diagnostic analysis. The result of the erosion operation 18 is a final binary map of the regions in the digitized image that are cytoplasm.

The next stage according to the invention, is the operation of the neural network at block 20. The neural network 20 is applied to the 8-bit digitized images, with attention restricted to those regions that lie within the cytoplasm as determined by the final binary cytoplasm map generated as a result of the previous operations. The neural network 20 makes decisions concerning the identity of individual picture elements (or "pixels") in the binary image as either being part of a nucleus or not part of a nucleus. The result of the operation of the neural network is a digital map of the regions within the cytoplasm that are considered to be nuclear material. The nuclear material map is then subjected to further processing. The neural network 20 according to the present invention is described in detail below.

Following the application of the neural network 20, the resulting nuclear material map is subjected to an erosion operation (block 22). The erosion operation 22 eliminates regions of the nuclear material map that are too small to be of diagnostic significance. The result is a modified binary map of nuclear regions.

The modified binary map resulting from the erosion operation 22 is then subjected to a dilation operation (block 24). The dilation operation 24 is subject to a no-join condition, such that, the dilation operation does not allow two separate regions of nuclear material to join to make a single region. In this way the accuracy of the binary map is preserved notwithstanding the dilation operation. The dilation operation 24 is preferably applied twice to ensure a proper filling of voids. The result of these dilation operations is a modified binary map of nuclear material.

Following the dilation operation 24, an erosion operation is applied (block 26). Double application of the erosion operation 26 eliminates regions of the nuclear material in the binary map that are too small to be of diagnostic significance. The result is a modified binary map of nuclear regions.

The remaining operations involve constructing a binary map comprising high gradients, i.e boundaries, of pixel intensity, in order to sever nuclear regions that share high gradient boundaries. The presence of these high gradient boundaries is evidence of two, closely spaced but separate nuclei.

The first step in severing the high-gradient boundaries in the nuclear map is to construct a binary map of these high gradient boundaries using a threshold operation (block 28) applied to a Sobel map.

The Sobel map is generated by applying the Sobel gradient operator to the 577 nm 8-bit digitized image to determine regions of that image that contain high gradients of pixel intensity (block 29). (The 8-bit digitized image for the 577 nm band was obtained from the levelling operation in block 12.) The result of the Sobel operation in block 29 is an 8-bit map of gradient intensity.

Following the threshold Sobel operation 28, a logical NOT operation is performed (block 30). The logical NOT operation 30 determines the coincidence of the two states, high-gradients and nuclei, and reverses the pixel value of the nuclear map at the point of the coincidence in order to eliminate it from regions that are presumed to be nuclear material. The result of this logical operation is a modified nuclear map.

The modified nuclear map is next subjected to an erosion operation (block 32). The erosion operation 32 eliminates regions in the modified nuclear map that are too small to be of diagnostic significance. The result is a modified binary map of nuclear regions.

After the application of the gradient technique for severing close nuclear boundaries (blocks 28 and 30) and the erosion operation (block 32) for clearing the image of insignificant regions, the binary map of nuclear regions is dramatically altered. To restore the map to its original boundaries while preserving the newly-formed separations, the process applies a dilation operation at block 34. The dilation operation 34 includes the condition that no two nuclear regions will become joined as they dilate and that no nuclear region will be allowed to grow outside its old boundary as defined by the binary map that existed before the Sobel procedure was applied. The dilation operation 34 is preferably applied four times. The result is a modified binary map of nuclear material.

With the application of the dilation operation 34, the nuclear segmentation procedure according to the multi-spectral segmentation process 1 is complete and the resulting binary nuclear map is labelled in block 36, and if required further image processing is applied.

As described above, the operation at block 20 in FIG. 1 comprises neural network processing of the digitized images. In general, the neural network 20 is a highly parallel, distributed, information processing system that has the topology of a directed graph. The network comprises a set of "nodes" and series of "connexions" between the nodes. The nodes comprise processing elements and the connexions between the nodes represent the transfer of information from one node to another.

Figure 2:
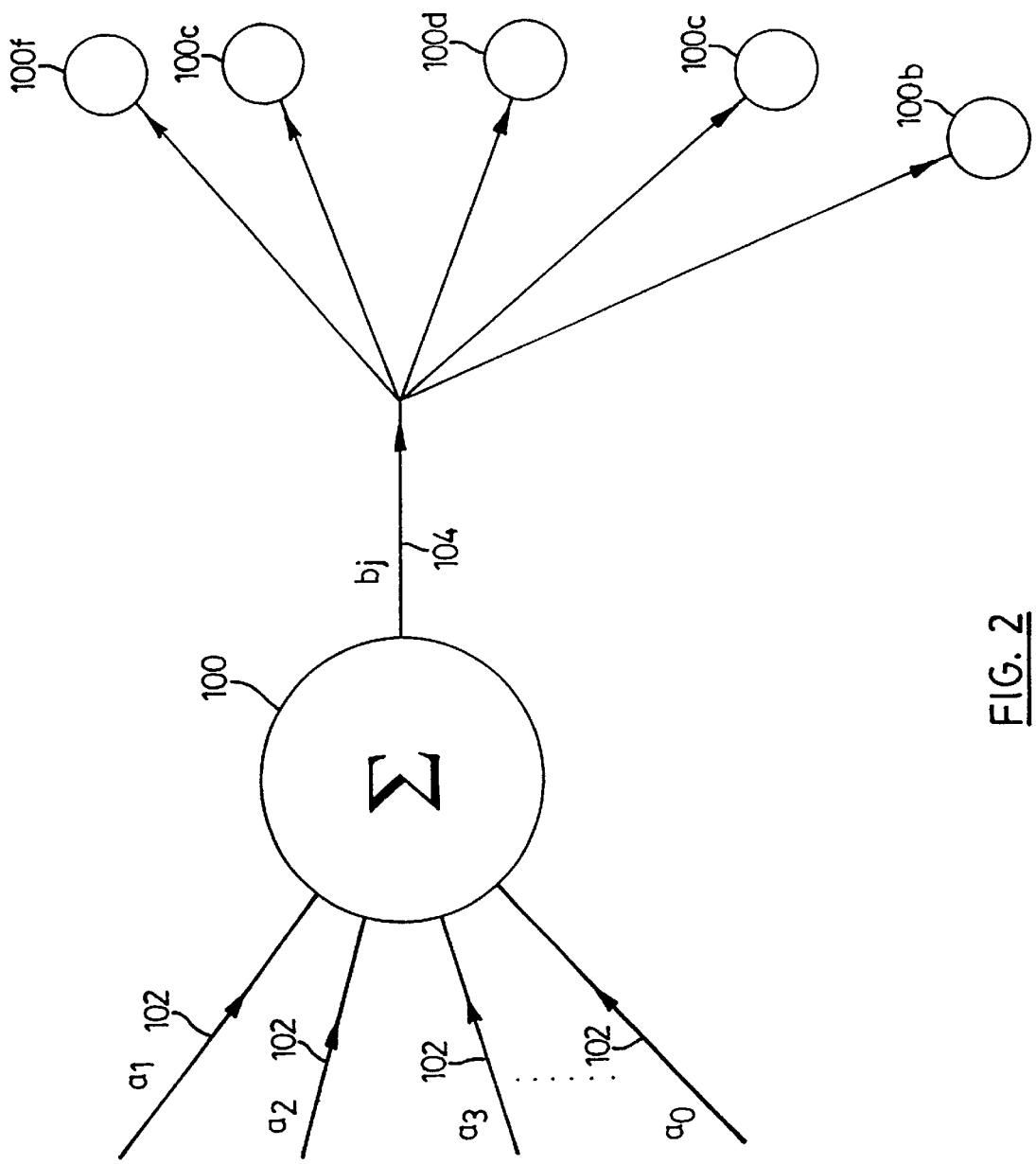
FIG. 2 shows in diagrammatic form a processing element for the neural network.

Reference is made to FIG. 2 which shows a node or processing element 100a for a backpropagation neural network 20. Each of the nodes 100a accepts one or more inputs 102 shown individually as $a_1, a_2, a_3 \ldots a_n$ in FIG. 2. The inputs 102 are taken into the node 100a and each input 102 is multiplied by its own mathematical weighting factor before being summed together with the threshold factor for the processing element 100a. The processing element 100a then generates a single output 104 (i.e. $b_j$) according to the "transfer function" being used in the network 20. The output 104 is then available as an input to other nodes or processing elements, for example processing elements 100b, 100c, 100d, 100e and 100f as depicted in FIG. 1.

The transfer function may be any suitable mathematical function but it is usual to employ a "sigmoid" function. The relationship between the inputs 102 into the node 100 and the output 104 is given by expression (1) as follows:

$$b_j = \{\Sigma w_{ji} a_i - \theta_j\}^{-1} \quad (1)$$

where $b_j$ is the output 104 of the node 100, $a_i$ is the value of the input 102 to the node labelled "I", $w_{ji}$ is the weighting given to that input 102, and $\theta_j$ is the threshold value for the node 100. In the present application, the transfer function is modelled after a sigmoid function.

Figure 3:
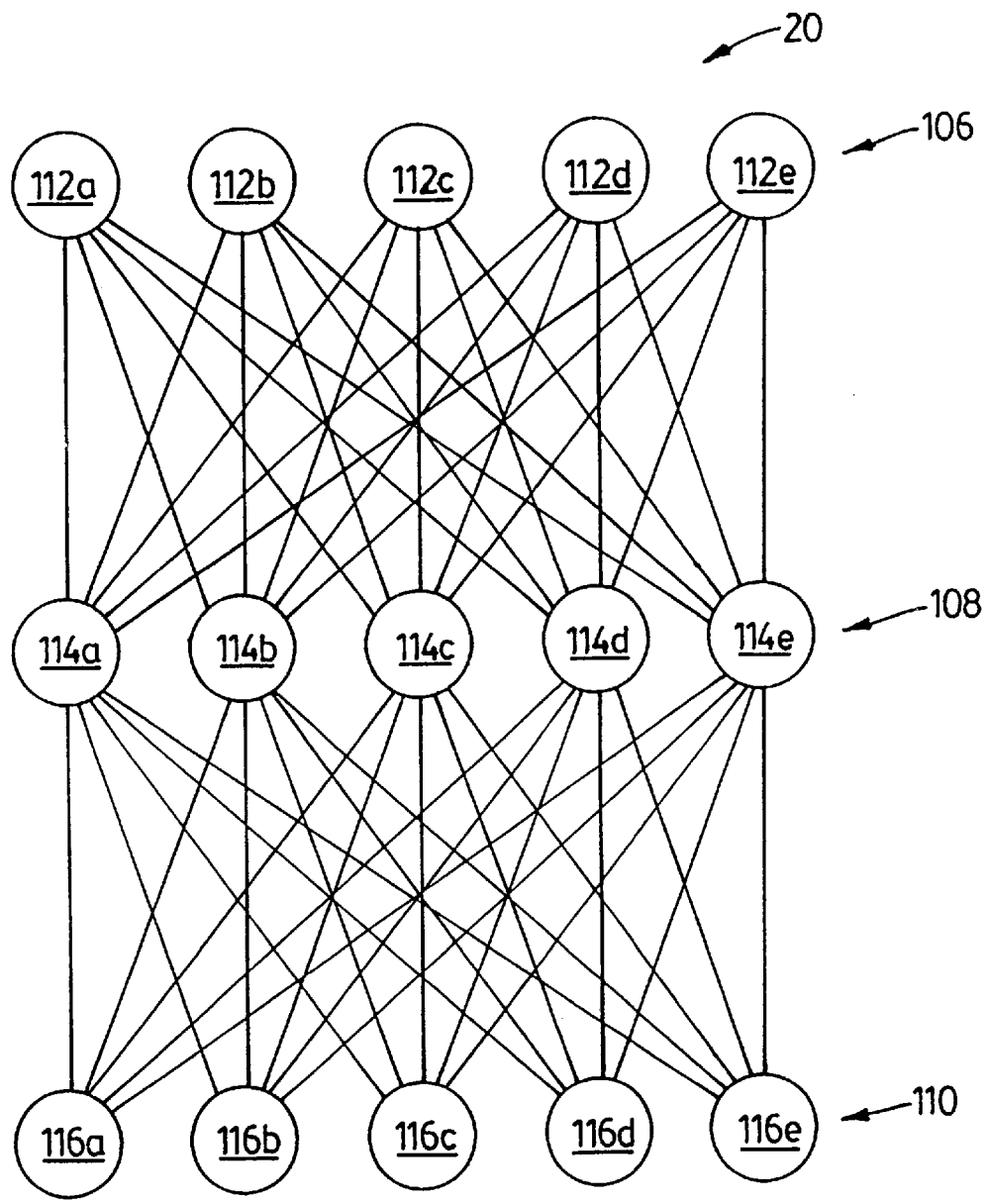
FIG. 3 shows in diagrammatic form a neural network comprising the processing elements of FIG. 2.

In its general form, the nodes or processing elements for the neural network are arranged in a series of layers denoted by 106, 108 and 110 as shown in FIG. 3. The first layer 106 comprises nodes or processing elements 112 shown individually as 112a, 112b, 112c, 112d and 112e. The first layer 106 is an input layer and accepts the information required for a decision.

The second layer 108 in the neural network 20 is known as the hidden layer and comprises processing elements 114 shown individually as 114a, 114b, 114c, 114d and 114e. All of the nodes 112 in the input layer 106 are connected to all of the nodes 114 in the hidden layer 108. It will be understood that there may be more than one hidden layer, with each node in the successive layer connected to each node of the previous layer. For convenience only one hidden layer 108 is shown in FIG. 3.

The (last) hidden layer 108 leads to the output layer 110. The output layer 110 comprises processing elements 116 shown individually as 116a, 116b, 116c, 116d and 116e in FIG. 3. Each node 114 of the (last) hidden layer 108 (FIG. 3) is connected to each node 116 of the output layer 110. The output layer 110 renders the decision to be interpreted by subsequent computing machinery.

The strength of the neural network architecture is its ability to generalize based on previous training of particular examples. In order to take advantage of this, the neural network is presented a series of examples of the type of objects that it is destined to classify. The backpropagation neural network organizes itself by altering the multiplicity of its connexion weights and thresholds according to its success in rendering a correct decision. This is called supervised learning wherein the operator provides the network with the information regarding its success in classification. The network relies on a standard general rule for modifying its connexion weights and thresholds based on the success of its performance, i.e. back-propagation.

In the context of the multi-spectral segmentation process, the multi-spectral images are divided into two classes: $C_o$—cytoplasm and $C_1$—nuclear, separated by the multi-dimensional threshold t which comprises a 3-dimensional space. The distribution of the pixels for the nuclear and cytoplasm objects is complex and the 3-D space comprises numerous clusters and non-overlapped regions. It has been found that the optimal threshold has a complex non-linear surface in the 3-D space, and the neural network according to the present invention provides the means for finding the complex threshold surface in the 3-D space in order to segment the nuclear and cytoplasmic objects.

According to this aspect of the invention, the neural network 20 comprises an input layer 106, a single hidden layer 108, and an output layer 110. The input layer 106 comprises three nodes or processing elements 112 (FIG. 3) for each of the three 8-bit digitized values for the particular pixel being examined. (The three digitized values arise from the three levelled images collected in each of the three optical bands, as described above with reference to FIG. 1.) The output layer 110 comprises a single processing element 116 (FIG. 3) which indicates whether the pixel under examination is or is not part. of the nucleus.

Before the neural network 20 can be successfully operated for decision-making it must first be "trained" in order to establish the proper combination of weights and thresholds. The training is performed outside of the segmentation procedure on a large set of examples. Errors made in the classification of pixels in the examples are "back-propagated" as corrections to the connexion weights and the threshold values in each of the processing units. Once the classification error is acceptable the network is "frozen" at these weight and threshold values and it is integrated as a simple algebraic operation into the segmentation procedure as shown at block 20 in FIG. 1.

In a preferred embodiment, the neural network 20 according to the invention comprises a Probability Projection Neural Network which will also be referred to as a PPNN. The PPNN according to the present invention features fast training for a large volume of data, processing of multimodal non-Gaussian data distribution, good generalization simultaneously with high sensitivity to small clusters of patterns representing the useful subclasses of cells. In another aspect, the PPNN is well-suited to a hardware-encoded implementation.

The PPNN according to the invention utilizes a Probability Density Function (PDF) estimator. As a result, the PPNN is suitable for use as a Probability Density Function estimator or as a general classifier in pattern recognition. The PPNN uses the training data to create an N-dimensional PDF array which in turn is used to estimate the likelihood of a feature vector being within the given classes as will now be described.

To create and train the PPN network, the input space is partitioned into m×m× . . . m discrete nodes (if the discrete input space is known, then m is usually selected less than the range). For example, for a 3-D PDF array creating a $2^6 \times 2^6 \times 2^6$ grid is sufficient.

Figure 4:
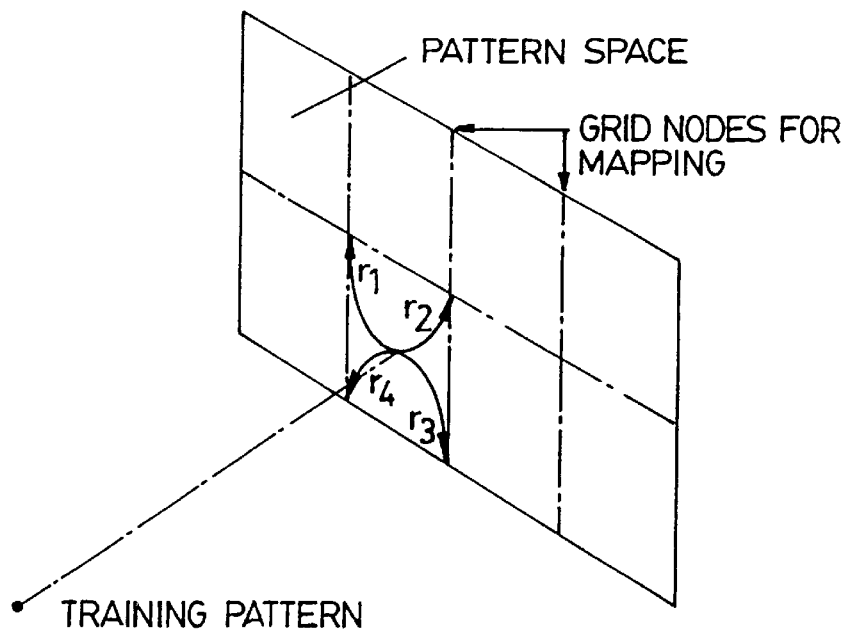
FIG. 4 shows in diagrammatic form a training step for the neural network.

As shown in FIG. 4, the next step involves mapping or projecting the influence of the each training pattern to the neighbour nodes. This is accomplished according to expression (2) as shown below:

$$P_j[x_0, x_1, \ldots, x_{n-1}] = P_{j-1}[x_0, x_1, \ldots, x_{n-1}] + d_j[x_0, x_1, \ldots, x_{n-1}];$$

$$d_j[x_0, x_1, \ldots, x_{n-1}] = \begin{cases} 1, & \text{if } r_k - 0 \\ 0, & \text{if } r_k \geq r_0 \\ \dfrac{1 - r_k}{\sum_{i=0}^{2^n - 1}(1 - r_i)}, & \text{if } r_k < r_0 \end{cases} \quad (2)$$

where $P_j[x_0, x_2, \ldots, x_{n-1}]$ is the current value of the $(x_0, x_1, \ldots, x_{n-1})$ node after the j'th iteration; $d_j[x_0, x_1, \ldots, x_{n-1}]$ represents the influence of j'th input pattern to the $(x_0,$ $x_1, \ldots, x_{n-1}$) node; $r_k$ is the distance from the pattern to the k'th node; $r_0$ is the minimum distance between two neighbour nodes; and n is the dimension of the space.

From expression (1), it will be appreciated that $$\forall j \sum_{k=1}^{2^n} d_{k(j)} = 1$$

represents the normalized values.

Once the accumulation of $P_N[x_0, x_1, \ldots, x_{n-1}]$ (where j=N–number of the training patterns) is completed, a normalization operation is performed to obtain the total energy value for PPNN $E_{PPN}=1$. The normalized values (i.e. P*) for PPNN are calculated according to expression (3) as follows:

$$P^*_N[x_0, x_1, \ldots, x_{n-1}] = P_N[x_0, x_1, \ldots, x_{n-1}]/N \quad (3)$$

For feed-forward calculations the trained and normalized nodes $P^*_N[x_0, x_1, \ldots, x_{M-1}]$ and the reverse mapping are utilized according to expression (4) given below, $$h_j[x_0, \ldots, x_{n-1}] = \sum_{i=0}^{2^n-1} P_N^{(i)}[x_0, x_1, \ldots, x_{n-1}] d_j^{(f)}[x_0, x_1, \ldots, x_{n-1}], \quad (4)$$

where $d_j^{(i)}[x_0, x_1, \ldots, x_{n-1}]$ are calculated according to expression (1) above.

To solve a two class (i.e. $C_0$—cytoplasm and $C_1$—nuclear) application using the PPNN according to the present invention, two networks must be trained for each class separately, that is, $P_{C0}[x_0, x_1, \ldots, x_{n-1}]$ and $P_{C1}[x_0, x_1, \ldots, x_{n-1}]$. Because both PPNN are normalized, they can be joined together according to expression (5) below as follows:

$$P_{C0/C1}[x_0, x_1, \ldots, x_{n-1}] = P^*_{C0}[x_0, x_1, \ldots, x_{n-1}] - P^*_{C1}[x_0, x_1, \ldots, x_{n-1}] \quad (5)$$

The final decision from expressions (4) and (5) is given by $$Pattern_j \in \begin{cases} C_0, & \text{if } h_j > 0 \\ C_1, & \text{if } h_j \leq 0 \end{cases} \quad (6)$$

While the PPNN according to the present invention is particularly suited to handle multi-modal data distributions, in many practical situations there will be an unbalanced data set. This means that some clusters will contain less data samples than other clusters and as a result some natural clusters which were represented with a small number of patterns could be lost after PPNN joining. To solve this problem there is provided an algorithm which equalizes all natural clusters according to another aspect of the invention.

Figure 5:
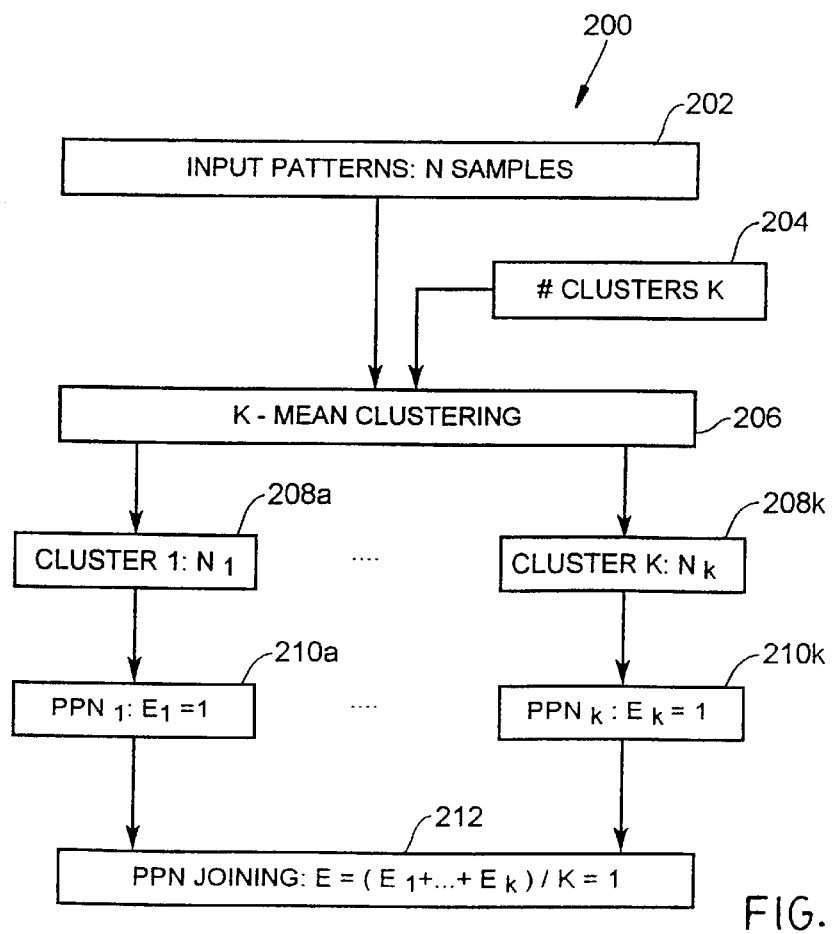
FIG. 5 shows in flow chart form a clustering algorithm for the neural network according to the present invention.

Reference is next made to FIG. 5, which shows in flow chart form an embodiment of a clustering algorithm 200 according to the present invention. All training patterns, i.e. N samples, in block 202 and a given number (i.e. "K") of clusters in block 204 are applied to a K-mean clustering operation in block 206. The clustering operation 206 clusters the input data and generates clusters 1 through K (block 208). Next, all the training data which belongs to an $i^{th}$-cluster is extracted into a separate sub-class. For each sub-class of training data, a normalized PPNN, i.e. $E_i=1$, is created (block 210). The final operation in the clustering algorithm comprises joining all of the K PPNN's together and normalizing the resulting PPNN by dividing all nodes by the number of clusters (block 212). The operation performed in block 212 may be expressed as follows:

$$E=(E_1+ \ldots +E_k)/K=1$$

It will also be understood that the clustering algorithm 200 may be implemented to the each class separately before creating the final classifier according the expression (6) above, as follows. The optimal number of clusters for each of two classes may be found from final PPNN performance analysis (expression (6) above). First, the number of clusters for $PPN_2=1$ are fixed and the optimal number of clusters for $PPN_1$ are found. Next, the reverse variant is modelled as: $PPN_1=1$, $\char`\^PPN_2=$opt. Lastly, the two optimal networks $PPN_1^{opt} \char`\^PPN_2^{opt}$ are combined together according to expression (6).

While the neural network assisted multi-spectral segmentation process is described with a Probability Projection Neural Network according to the present invention, it will be understood that other conventional neural networks are suitable, including for example, Backpropagation (BP) networks, Elliptic Basic Functions (EBF) networks, and Learning Vector Quantization (LQV) networks. However, the PPNN is preferred. The performance results of the Probability Projection Neural Net have been found to exceed those achieved by conventional networks.

According to another aspect of the present invention, the neural network assisted multi-spectral segmentation process is implemented as a hardware-encoded procedure embedded in conventional FPGA (Field Programmable Gate Array) logic as part of a special-purpose computer.

Figure 6:
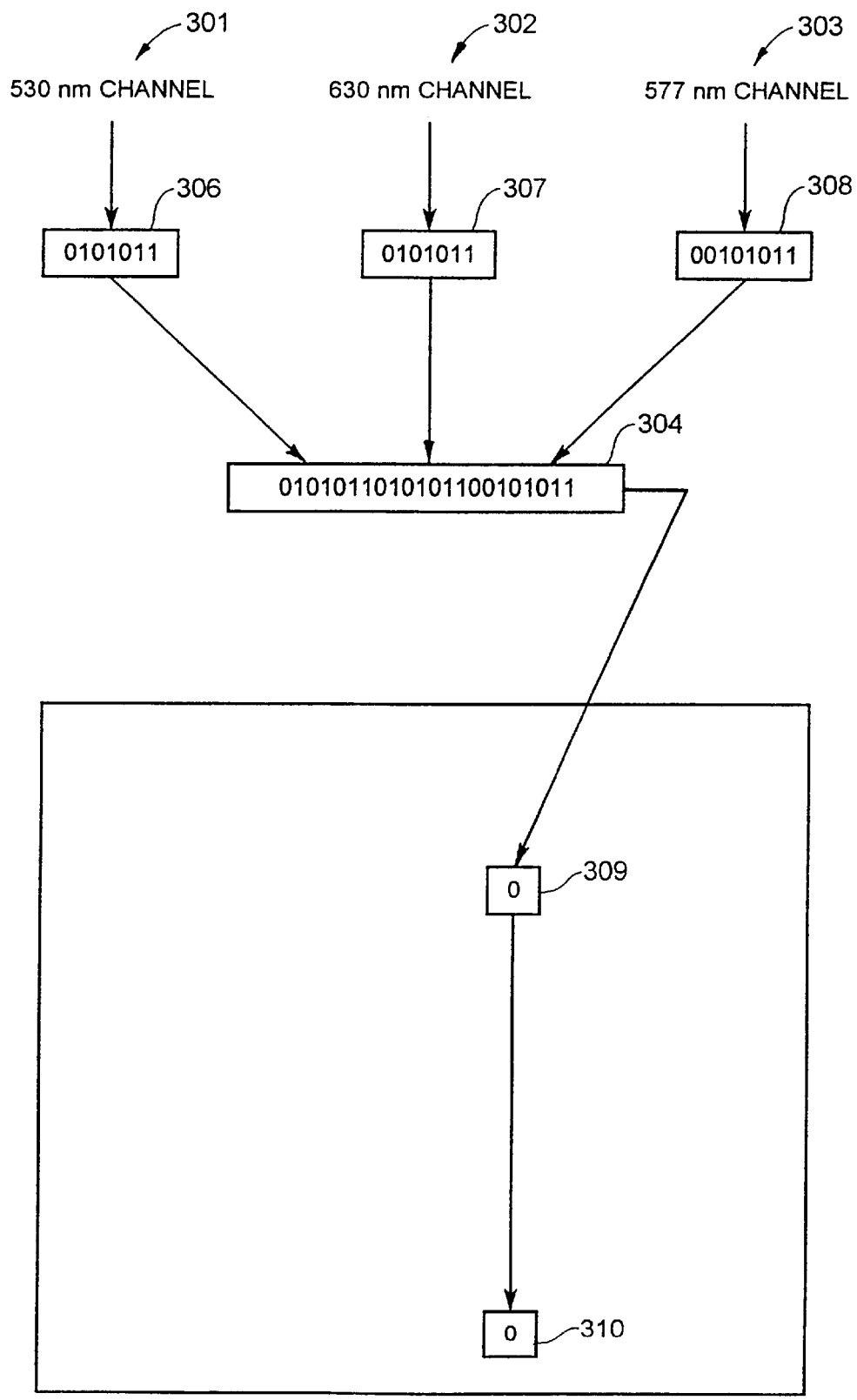
FIG. 6 shows a hardware implementation for the neural network according to the present invention.

The hardware implementation of this network is found in the form of a look-up table contained in a portion of hardware memory (FIG. 6). As described above, the neural network 20 comprises three input nodes and a single, binary output node. The structure of the neural network 20 according to the present invention also simplifies the hardware implementation of the network.

As shown in FIG. 6, the three input nodes correspond to three optical bands 301, 302, 303 used in gathering the images. The images taken in the 530 nm and 630 nm bands have 7-bits of useful resolution while the 577 nm band retains all 8-bits. (The 577 nm band is centered on the nucleus.) The performance of the neural network 20 is then determined for all possible combinations of these three inputs. Since there are 22 bits in total, there are $2^{22}$ or 4.2 million possible combinations. To create the look-up table, all input pixels in the space ($2^7 \times 2^7 \times 2^8$ variants for the three images in the present embodiment) are scanned and the look-up table is filled with the PPNN decision, i.e. 1—pixel belongs to nuclear; 0—pixel doesn't belong to nuclear, for all each of these pixel combinations.

The coding of the results (i.e. outputs) of the neural network comprises assigning each possible combination of inputs a unique address 304 in a look-up table 305 stored in memory. The address 304 in the table 305 is formed from by joining together the binary values of the three channel values indicated by 306, 307, 308, respectively in FIG. 6. For example, as shown in FIG. 6, the pixel for the image from the first channel 301 (i.e. 530 nm) is binary 0101011, the pixel for image from the second channel 302 (i.e. 630 nm) is binary 0101011, and the pixel for the image from the third channel 303 (i.e 577 nm) is binary 00101011, and concatenated together binary representations 306, 307, 308 form the address 304 which is binary 01010110101011001011. The address 304 points to a location in the look-up table 305 (i.e. memory) which stores a single binary value 309 that represents the response of the neural network to this combination of inputs, e.g. the logic 0 at memory location 01010110101011001011011 signifies that the pixel in question does not belong to the nucleus.

The hardware-encoding of NNA-MSS advantageously allows the process to execute at a high speed while making a complex decision. Secondly, as experimental data is further tabulated and evaluated more complex decision spaces can be utilized to improve segmentation accuracy. Thus, an algorithm according to the present invention can be optimized further by the adjustment of a table of coefficients that describe the neural-network connexion weights without the necessity of altering the system architecture.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method for segmenting nuclear and cytoplasmic objects in a cellular specimen, said method comprising the steps of:
    (a) acquiring a plurality of narrow band images of said cellular specimen, said narrow band images comprising a first image captured in an optical band ranging from 535 nm to 545 nm, a second image captured in an optical band ranging from 572 nm to 582 nm, and a third image captured in an optical band ranging from 625 nm to 635 nm and wherein said cellular specimen is subjected to a Pananicolaou staining procedure;
    (b) identifying cellular material from said narrow band images and creating a cellular material map, including a threshold operation for identifying regions in said images containing cellular material;
    (c) applying dilation and erosion operations to said cellular material map; and
    (d) applying a neural network to said cellular material map to segment nuclear objects and cytoplasmic objects in said narrow band images and including examining said narrow band images on a pixel by pixel basis to distinguish said nuclear objects from said cytoplasmic objects.

2. A method for segmenting nuclear and cytoplasmic objects in a cellular specimen, said method comprising the steps of:
    (a) acquiring a plurality of narrow band images of said cellular specimen;
    (b) identifying cellular material from said narrow band images and creating a cellular material map; and
    (c) applying a neural network to said cellular material map to segment nuclear objects and cytoplasmic objects in said narrow band images;
    (d) wherein said step of applying a neural network comprises determining a threshold surface in three-dimensional space, and said nuclear and cytoplasmic objects being separated by said three dimensional space.

3. The method as claimed in claim 2, wherein said neural network comprises a probability projection neural network.

4. The method as claimed in claim 3, wherein said probability projection neural network utilizes a probability density function estimator to estimate a feature vector being within given classes.

5. The method as claimed in claim 4, further including the step of equalizing clusters of data appearing in said images.

6. A system for identifying nuclear and cytoplasmic objects in a cellular specimen, said system comprising:
    (a) image acquisition means for acquiring a plurality of narrow band images of said cellular specimen;
    (b) processing means for processing said narrow band images and generating a cellular material map identifying cellular material;
    (c) processor means for processing said cellular material map and including means for segmentation of nuclear objects and cytoplasmic objects in said narrow band images;
    (d) said processor means including a look-up table stored in memory having decision outputs stored in addressable locations of said memory, and including addressing means for generating an address to said memory for reading said decision output corresponding to a combination of said image inputs.

7. The system as claimed in claim 6, wherein said addressing means comprises means for combining binary values corresponding to said images and forming an address for accessing said memory from said combined binary values.

8. A system for identifying nuclear and cytoplasmic objects in a cellular specimen, said system comprising:
    (a) image acquisition means for acquiring a plurality of narrow band images of said cellular specimen;
    (b) processing means for processing said narrow band images and generating a cellular material map identifying cellular material;
    (c) neural processor means for processing said cellular material map, including a probability projection neural network, and having means for segmentation of nuclear objects and cytoplasmic objects in said narrow band images, a probability density function estimator to estimate a feature vector beam within given classes, and equalization means for equalizing clusters of data in said images.

9. A system for identifying nuclear and cytoplasmic objects in a cellular specimen, said system comprising:
    (a) image acquisition means for acquiring a plurality of narrow band images of said cellular specimen;
    (b) processing means for processing said narrow band images and generating a cellular material map identifying cellular material;
    (c) neural processor means for processing said cellular material map and including means for segmentation of nuclear objects and cytoplasmic objects in said narrow band images and means for determining threshold surface in three-dimensional space, said nuclear and cytoplasmic objects being separated by said three-dimensional space.

10. A hardware-encoded processor for segmenting nuclear objects and cytoplasmic objects in cellular specimens based on a plurality of digitized narrow band images of said cellular specimen, said hardware-encoded processor comprising:
    (a) a memory having a plurality of addressable storage locations;
    (b) said addressable storage locations containing segmentation information associated with the cellular specimen;
    (c) address generation means for generating an address from the digitized narrow band images for a cellular specimen for accessing the segmentation information stored in said memory representative of the cellular specimen.

11. The hardware-encoded processor as claimed in claim 10, wherein said digitized narrow band images comprise a first image in an optical band ranging from 535 nm to 545 nm, a second image in an optical band ranging from 572 nm to 582 nm, and a third image in an optical band ranging from 625 nm and 635, nm, and wherein the cellular specimen is subjected to a Papanicolaou staining procedure.

12. The hardware-encoded processor as claimed in claim 11, wherein said segmentation information comprises a binary digit stored in each of said addressable locations of said memory, one state of said binary digit indicating that said cellular specimen comprises a nuclear object, and the other state of said binary digit indicating that said cellular specimen comprises a cytoplasmic object.

13. The system as claimed in claim 8, wherein said neural processor means includes means for examining said narrow band images on a pixel by pixel basis to distinguish said nuclear objects from said cytoplasmic objects.

14. The system as claimed in claim 13, wherein said image acquisition means includes means for capturing a first image in an optical band ranging from 535 nm to 545 nm, means for capturing a second image in an optical band ranging from 572 nm to 582 nm, and means for capturing a third image in an optical band ranging from 625 nm to 635 nm, and wherein the cellular specimen is subjected to a Papanicolaou staining procedure.

* * * * *